April 2, 1963 G. J. VON ABRAMS Plant Pat. 2,246
ROSE PLANT
Filed April 16, 1962
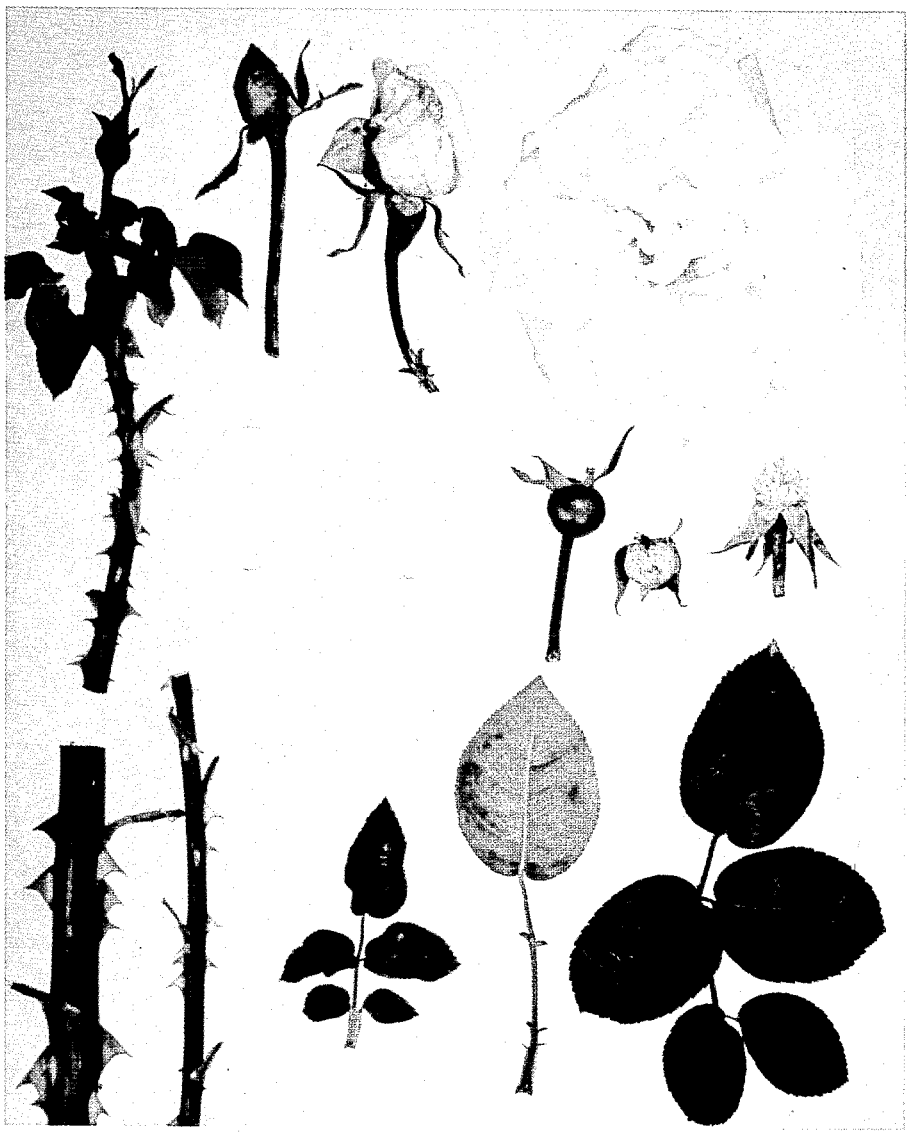
INVENTOR.
GORDON J. VON ABRAMS
BY R. R. Geiler.
ATTORNEY United States Patent Office Plant Pat. 2,246
Patented Apr. 2, 1963

2,246
ROSE PLANT

Gordon J. Von Abrams, 3463 NW. Savier St., Portland, Oreg.

Filed Apr. 16, 1962, Ser. No. 187,998
1 Claim. (Cl. 47—61)

This invention comprises a new and distinct variety of rose plant of the commercial "hybrid tea" class. In the pollination which took place in the breeding of this new variety of rose plant the seed parent (unpatented) had been produced by crossing the rose variety "Blanche Mallerin" (Plant Patent No. 594) with the rose variety "Peace" (Plant Patent No. 591), and the pollen parent (an unpatented variety not in commerce) resulted from the crossing of the rose variety "Peace" with the rose variety "Frau Karl Druschki" (unpatented). The pollination for the breeding of this new variety occurred in the spring of 1951 at Scappoose, Oregon.

The main objective of this particular breeding was to produce a new variety of rose plant which would bear large white or near-white, flowers of excellent form and heavy petalage, and a plant of vigorous sturdy habit. This objective was achieved and the features of distinctiveness of this new variety consist mainly in the combination of flower color and flower form, the many petals in the flower, the heavy foliage of the plant, and the vigorous plant habit.

This new variety of rose plant is a seedling, tall bush type, suitable for use outdoors either for garden decoration or for cut flowers.

This new rose plant has been propagated asexually at Scappoose, Oregon, by bud-grafting and has been shown to retain its distinguishing characteristics through successive propagations by bud-grafting.

This new variety is clearly distinct from its parent varieties, the flower being more nearly white than either. The flower of the new variety is larger and has more petals than that of the seed parent. The plant is larger than that of the seed parent, smaller than that of the pollen parent.

The plant is also taller and larger than that of the "White Knight" (Plant Patent No. 1,359), "Virgo" (unpatented) or "Blanche Mallerin" (Plant Patent No. 594), and the flower of this new plant has more petals but is usually less white than the flowers of these three varieties.

The plant blooms moderately abundantly outdoors and blooms nearly continuously during the growing season. The flowers are borne usually one on a long strong stem although sometimes there may be as many as 4 or 5 per stem. The general color effect is near-white, but a more detailed color description follows.

The accompanying illustration shows the flower in different stages together with various portions of the plant, the colors shown being as nearly true as is reasonably possible in color reproduction of this type. The specimens shown and described were propagated and grown at Scappoose, Oregon.

In the detailed description which follows, the following color references are used:

(1) Wilson, R. F.: Royal Horticultural Society Colour Chart, England, 1940. Abbreviated "W."

(2) Ridgway, R.: Color Standards and Color Nomenclature, Washington, D.C., 1912. Abbreviated "R."

*Flowers*

Open flower:

*Size.*—Large (11 to 15 cm.).

*Petalage.*—Very double (i.e.—80 petals).

*Form.*—At first nearly globular. As the outer petals expand and reflex, the center appears somewhat depressed, as the contorted and compressed center petals tend to remain tightly clasped.

*Fragrance.*—Light.

Petals:

*Substance.*—Medium thin, soft, flexible.

*Texture.*—Outside—satiny, quite smooth. Inside—satiny.

*Shape and size (in open flower).*—Outside petal—broadly obovate, near-orbicular, with width nearly as great, sometimes greater than length (i.e.—5.5 x 5.5 cm.). Intermediate petal—obovate (i.e.—3 cm. wide x 4 cm. long). Inside petal—irregular, generally near-narrow obovate.

Color: Following description of newly opened flower made in July 1961 from specimens grown outdoors near Scappoose, Oregon:

*Newly open—outside petal.*—Outer surface—near-white, with small flush at base near, or lighter than, Pale Greenish Yellow (R. 25. YG-Y. *d*, Plate V). Inner surface—near-white, with flush at base near Pale Lemon Yellow (R. 23. YELLOW, Plate IV).

*Intermediate petal.*—As outside petal, but with basal flush slightly more intense and slightly larger, spreading upward along "veins."

*Inside petal.*—Outer surface—creamy white, lighter than Massicot Yellow (R. 21′. O-YY. *f*, Plate XVI) with small flush at base near Pale Lemon Yellow (R. 23 YELLOW, Plate IV). Inner surface—lighter than Barium Yellow (R. 23′. YELLOW. *d*, Plate XVI) with flush at base near Lemon Yellow (R. 23. YELLOW, Plate IV).

*General color effect (of the newly open flower).*—Pale creamy white, near Primrose Yellow (W. 601/2 to 601/3, p. 65).

The following is a description of a flower open three days in July 1961, on a plant grown near Scappoose, Oregon.

*Outside petal.*—Outer surface—white or near-white; very pale yellow flush at base. Inner surface—white or near-white with flush at base near Picric Yellow (R. 23, YELLOW. *d*, Plate IV) or lighter.

*Intermediate petal.*—Outer surface—white or near-white; very pale yellow flush at base. Inner surface—white or near-white, with flush at base near Picric Yellow (R. 23. YELLOW. *d*, Plate IV) or lighter.

*Inside petal.*—Outer surface—white or near-white, very pale yellow flush at base. Inner surface—white or near-white, with flush at base near Picric Yellow (R. 23. YELLOW. *d*, Plate IV) or lighter.

*General color effect.*—Near-white, or with pale yellow undertone.

Flower behavior: Under some circumstances, the flower shows almost no yellow pigment, and appears very white. In hot dry weather, the petals may "burn" at the apical margins. In cold wet weather, the bloom may open very slowly, sometimes "balling."

Flower longevity: Very good for this color range.

Bud:

*Peduncle.*—Medium-long, large, erect. Surface with numerous glandular cilia. Color light green, near Lettuce Green (W. 861/2, p. 176).

*Sepals.*—Large (i.e., 14 x 28 mm.); spear shape, with ordinary acuminate point. Margins with few bristle-like appendages and several glandular cilia. Inner surface tomentose, grayish; outer surface glossy, somewhat rugose, color near Scheeles Green (W. 860/1, p. 175). Behavior—reflex.

*As calyx breaks.*—Size—medium; short-pointed; terminal points moderate. Exposed petal color—greenish white, sometimes with reddish flush.

*As first petal opens.*—Size of bud—medium-large (i.e., 3 x 4.5 cm.). Form of bud—pointed, tapered but not slender. Color of petal: outer surface—near white; Pale Greenish Yellow (R. 25. YG-Y. *d*, Plate V) flush at base; inner surface—near white, with near Lemon Yellow (R. 23. YELLOW, Plate IV) flush at base.

*Opening habit.*—Opens well under most weather conditions. May "ball" in cold wet weather.

*Plant*

Foliage:

*Leaves.*—Abundant; large, compound, usually of 5 leaflets.

*Leaflets.*—Substance—thick, hard, stiff. Texture—medium smooth, glossy. Size—large (i.e., 6.5 x 8 cm.). Shape—broadly ovate; base cordate; apex acuminate; margin serrate.

*Color.*—Mature: upper surface—darker than Parsley Green (W. 00962, page 193); under surface—near Asphodel Green (R. 29'''. GG-Y., Plate XLI). Young: upper surface—near Cerro Green (R. 27. G-Y. *m*, Plate V), often flushed maroon and appearing much darker; under surface—near Asphodel Green (R. 29'''. GG-Y., Plate XLI) heavily flushed maroon.

*Rachis.*—Heavy, with several thorns on lower side.

*Stipules.*—Size medium, somewhat slender. Margins with numerous glandular cilia. Points short; nearly straight; set at an angle greater than 45°, nearly perpendicular to rachis.

*Disease resistance.*—Ordinary.

Growth:

*Habit.*—Tall, upright, full.

*Vigor.*—Strong.

*Canes (2nd year growth).*—Caliber—large to very large. Surface—corky; thorns—numerous; medium; hooked downward; grayish. Color—grayish green.

*Main stems (of current year's growth).*—Caliber—large. Surface—quite smooth; thorns—numerous; medium size; hooked strongly downward; brown to grayish-brown. Color—grayish green.

*Branches (currently bearing senescent flowers).*—Caliber—medium (i.e., at upper internode—4 mm.). Surface—somewhat glaucous; thorns—several; medium to small; hooked downward, light tan to brown; cilia—few to several; glandular. Color—near between Courage Green (R. 25'. YG-Y. *i*, Plate XVII) and Light Hellebore Green (R. 25'. YG-Y. *k*, Plate XVII).

*New shoots (in rapid growth).*—Surface—somewhat glaucous; thorns—several small to medium, hooked sharply downward, color near Pompeian Red (R. 3'. O-R. *i*, Plate XIII); cilia—very few; glandular. Color—near Biscay Green (R. 27'. G-Y. *i*, Plate XVII) unilaterally flushed, to entirely, near-Prussian Red (R. 5''. OO-R. *k*, Plate XXVII).

*Reproductive Organs*

Stamens: Quantity—moderate. Ordinary. Pollen viable and moderately abundant.

Pistils:

*Quantity.*—Moderate.

*Styles.*—Free; ordinary; base embedded in cottony tissue.

*Stigmas.*—Small, grayish.

*Ovaries.*—Enclosed.

Receptacle and calyx tube:

*Size.*—Medium (i.e.—1.5 cm. diameter x 1 cm. high).

*Shape.*—Ordinary, slightly turbinate.

*Disc.*—Prominent, rounded.

*Surface.*—Slightly glaucous.

Seed pod:

*Quantity.*—Sparse to moderate.

*Size.*—Large.

*Shape.*—Globose, slightly depressed.

*Sepals.*—Persist.

*Surface.*—Quite smooth, glossy. Several gland-cilia near base.

*Wall.*—Thick, fleshy.

*Color.*—Variable orange.

Seeds: Few, large, normal.

Having thus described my invention, I claim:

A new and distinct variety of rose plant of the commercial "hybrid tea" class, substantially as herein shown and described, characterized by its white and near-white color, its large, well formed flowers and heavy petalage, and its vigorous plant habit.

No references cited.